United States Patent
Larson et al.

(12) 
(10) Patent No.: US 6,309,380 B1
(45) Date of Patent: Oct. 30, 2001

(54) DRUG DELIVERY VIA CONFORMAL FILM

(76) Inventors: Marian L. Larson, 214 Baywood Dr., Newport Beach, CA (US) 92660; Eugene A. Larson, 2457 W. Shore Dr., Lummi Island, WA (US) 98262

(*) Notice: Subject to any disclaimer, the term of this patent is extended or adjusted under 35 U.S.C. 154(b) by 0 days.

(21) Appl. No.: 09/238,946

(22) Filed: Jan. 27, 1999

(51) Int. Cl.⁷ .................................................... A61M 31/00
(52) U.S. Cl. ........................... 604/502; 604/28; 604/265; 128/898
(58) Field of Search ................................. 604/28, 264, 265, 604/174, 175, 96 A, 891.1, 500, 502; 128/898; 606/192, 194; 424/422–423; 427/2.1

(56) References Cited

U.S. PATENT DOCUMENTS

| | | |
|---|---|---|
| 4,886,062 | 12/1989 | Wiktor . |
| 4,994,033 | 2/1991 | Shockey et al. . |
| 5,334,640 * | 8/1994 | Desai et al. ............................. 524/56 |
| 5,410,016 * | 4/1995 | Hubbell et al. ....................... 528/354 |
| 5,443,458 | 8/1995 | Eury . |
| 5,500,013 | 3/1996 | Buscemi et al. . |
| 5,545,208 | 8/1996 | Wolff et al. . |
| 5,551,954 | 9/1996 | Buscemi et al. . |
| 5,605,696 | 2/1997 | Eury et al. . |
| 5,674,192 * | 10/1997 | Sahatjian et al. ....................... 604/28 |
| 5,766,710 | 6/1998 | Turnlund et al. . |
| 5,769,883 | 6/1998 | Buscemi et al . |
| 6,005,020 * | 12/1999 | Loomis ................................ 523/105 |

* cited by examiner

*Primary Examiner*—Anhtuan T. Nguyen
*Assistant Examiner*—Michael M Thompson
(74) *Attorney, Agent, or Firm*—Robert L. McDowell

(57) ABSTRACT

A drug delivery conformal film system according to the present invention is adapted to be compounded and applied, by medical personnel at the point of use, to a medical device such as a cardiovascular and urology stent, pacemaker, vascular graft, suture ring of mechanical heart valve, implantable infusion port, implantable drug delivery pump, orthopedic hardware and appliance, and, neurological stimulating device. The drug delivery conformal film consists of one of three in vivo biocompatible; biodegradable, bioerodable or bioabsorbable embodiments: (1) cross-linked sodium alginate, (2) UV photo-active polymer, or, (3) hydrogels. An implantable medical device such as the stent or suture ring of a mechanical artificial heart valve is coated with an in vivo biocompatible; biodegradable or bioerodable or bioabsorbable solution comprising a polymer and containing a drug, the solution is cross-linked or cured to form a film on the device immediately prior to placement in the body. When the coated device is introduced into the body, the drug contained in the coating is released in a local region. The invention provides a point of use in vivo drug delivery system whereby the drug and its concentration can be selected by medical personnel immediately prior to implantation of the medical device.

17 Claims, No Drawings

DRUG DELIVERY VIA CONFORMAL FILM

FIELD OF THE INVENTION

The present invention relates to the local delivery of drugs in vivo into the cardiovascular system and other body regions. In particular, the present invention is directed to the local delivery of drugs by applying a coating of a bioabsorbable/biodegradable or inert, in vivo biocompatible conformal film, to an implantable medical device.

BACKGROUND OF THE INVENTION

Angioplasty is a procedure that involves placing and inflating a balloon catheter in the blood vessel in the area of blockage, which breaks up the accumulated plaque and opens the vessel. While this technique works well in the short term, current literature indicates that 30 to 50% of all angioplasty operations performed will need follow-up treatment within six months. This is due to incomplete plaque removal and the formation of scar tissue as a result of irritation of the blood vessel, known as restenosis. Restenosis results in significant morbidity and mortality and often necessitates further interventions such as repeat angioplasty , coronary bypass, laser surgery or local drug delivery. There has been a focused effort in the health-care industry over the last few years to combat restenosis because repeat angioplasty or surgery is expensive, inconvenient, and potentially life threatening.

Limitations of angioplasty long-term success include abrupt closure (4.4–8.3%) and restenosis (chronic reclosure 30–50%) of the vessel—both of which are associated with excessive vascular injury.

Intravascular stenting (the placement of a supporting structure within a blood vessel) has demonstrated moderate success in addressing these issues. These devices provide structural support to keep the vessel walls from closing and minimize the problem of arterial blockage caused by plaque falling in to the vessel after inflation.

Stents have been made using materials of varied composition. U.S. Pat. No. 4,886,062 to Wiktor describes a stent made from low memory metal such as a copper alloy, titanium, or gold. Current stent designs tend to be thrombogenic (causing clot formation) and immunologically stimulating (causing cell formation). Current metal stent designs will not eliminate the restenosis problem. If restenosis should recur, follow-up treatments such as laser surgery or localized drug delivery using other angioplasty devices may be required. A stent alone can not restrict hyperplasia of smooth muscle cells, nor can it prevent restenosis or thrombus. Local delivery of antithrombogenic drugs and those capable of restricting hyperplasia of smooth muscle cells is desirable.

Drugs have been incorporated on or in a catheter or stent during the manufacturing design to provide local delivery of drugs to address restenosis, thrombus, and coagulation. U.S. Pat. No. 4,994,033 to Shockey et al.; U.S. Pat. No. 5,674,192 to Sahatjian et al. and U.S. Pat. No. 5,545,208 to Wolff et al. disclose catheters comprising absorbable/biodegradable polymers or hydrogels containing the desired dosage of a drug . Stents incorporating drug delivery may be found, for example, in U.S. Pat. No. 5,766,710 to Tumiund et al.; U.S. Pat. No. 5,769,883 to Buscemi et al.; U.S. Pat. No. 5,605, 696 to Eury et al.; U.S. Pat. No. 5,500,013 to Buscemi et al.; U.S. Pat. No. 5,551,954 to Buscemi et al. and U.S. Pat. No. 5,443,458 to Eury.

When drugs or biological modifiers are applied in conjunction with the manufacture of the device, there are several problems, for example:

1. sterilization: heat or ionizing radiation alters the composition of many drugs and biological modifiers;
2. the presence of a drug imposes a shorter shelf life independent of the implantable medical device, and could require special storage (i.e. refrigeration);
3. the drug dosage is not variable for specific patient needs; and,
4. a large inventory of devices is required to provide a range of drugs and therapies.

It is an object of the present invention to provide a drug delivery system that overcomes the deficiencies associated with the application of drugs in conjunction with the manufacture of the device.

It is a further object of the present invention to provide a procedure where the drug is applied to the device at the point of use of the device.

SUMMARY OF THE INVENTION

The present invention is directed to a method of producing an implantable drug-deliverable medical device. The method comprises providing an implantable medical device, coating the device with an in vivo biocompatible and biodegradable or bioabsorbable or bioerodable liquid or gel solution containing a polymer with the solution comprising a desired dosage amount of one or more predetermined drugs. The solution is converted to a film adhering to the medical device thereby forming the implantable drug-deliverable medical device.

The present invention is also directed to a drug delivery conformal film system adapted to be applied by medical personnel at the point of use, to an implantable medical device such as cardiovascular and urology stents, pacemakers, vascular grafts, suture rings of mechanical heart valves, implantable injection or infusion ports, implantable drug delivery pumps, orthopedic hardware and appliances, and, neurological stimulating devices. The drug delivery conformal film comprises one of three in vivo biocompatible; biodegradable, bio-erodable or bio-inert embodiments: (1) cross-linked sodium alginate, (2) UV photo-active polymer, or, (3) hydrogels. A stent or other implantable medical device such as the suture ring of a mechanical artificial heart valve is coated with this biodegradable, bio-erodable or bio-inert material containing a drug, cross-linked or cured, or otherwise treated to form a film, immediately prior to placement in the body. When the film-coated device is introduced into the body, the drug contained in the film coating is released in a local region. The invention provides a point of use in vivo drug delivery system whereby the drug and its concentration can be selected by medical personnel immediately prior to implantation of the medical device.

DETAILED DESCRIPTION OF THE PREFERRED EMBODIMENTS

The present invention will now be discussed in detail with reference to the preferred embodiments. Unless otherwise stated, all percentages represent weight percent.

Drugs or other biologically active materials incorporated into the drug delivery conformal film system of the present invention are intended to perform a variety of functions, including, but not limited to: anti-clotting or anti-platelet formation, and the prevention of smooth muscle cell growth on the vessel wall. Drugs anticipated for delivery include antibiotics, anticoagulants, tissue generation factor, and angiogenesis drugs. Drugs also include, but are not limited to, anti-thrombogenic drugs (heparin, PPACK, enoxaprin, aspirin, coumadin, hirudin, TPA, urokinase, and streptokinase), anti-proliferative drugs (monoclonal antibodies, heparin, angiopeptin, enxoaprin, methotrexate, cisplatin, flourouracil, Adriamycin), antimetabolites, thromboxane inhibitors, non- steroidal and steroidal anti-inflammatory drugs, Beta and Calcium channel blockers, genetic materials (including DNA and RNA fragments), and bioactive materials (such as fibronectin, laminin, elastin, collagen, and intergrins).

As stated previously, the drug delivery conformal film of the present invention comprises one of three in vivo biocompatible; biodegradable, bio-erodable or bio-inert embodiments: (1) cross-linked sodium alginate, (2) UV photo-active polymer, or, (3) hydrogels, for example, thermal irreversible hydrogels. Of these embodiments, cross-linked sodium alginate is preferred.

Sodium alginate is preferred because of its biocompatibility and in vivo biodegradability, and cross-linking film forming properties. A sterile and low endotoxin form of sodium alginate has recently become available under product number K8P569 from Monsanto, 800 N. Lindbargh Blvd. St. Louis, Mo., or under product number UP MVG from Pro Nova, Strandveien 18, N-1324 Lysaker, Norway. Very low endotoxin levels can be obtained in alginates by use of a highly specialized purification process. Alginates in a water gel form have the unique ability to form elastic films by reaction with calcium salts and/or magnesium salts. Once cross-linked, these films retain their shape and resist stress.

The preferred embodiment of the present invention is a medical release drug delivery conformal film system comprised of sterile, low endotoxin sodium alginate and sterile low-pyrogen water which uses a solution of calcium chloride to achieve gelation through cross-linking. The sodium alginates selected for this invention have a Mannuronic acid content of approximately 58 to 62% and a Guluronic acid content of approximately 42 to 38%. The alginate films thus produced have known and acceptable long-term biocompatibility and biodegradability in vivo and are manufactured in such a manner and form that renders the film sterile and biocompatible with human tissue, organs and body fluids. Sodium alginate in purified form, such as Monsanto part number K8P569 and ProNova part number UP MVG as a solution in water containing acceptably low levels of pyrogens is the preferred composition that demonstrates the desired in vivo biocompatibility and known in vivo biodegradability.

Alginates, such as sodium alginate, form aqueous solutions in either liquid or gel form. The addition of increasing amounts of non-aqueous water-miscible solvents (i.e., glycols) to an alginate solution increases the solubility of non-water-soluble compounds. As the alginate solution in this invention is intended to serve as a drug delivery film, non-water soluble drugs can be added to an alginate solution prepared with up to 10% propylene glycol, or other biocompatible solvents, substituted for water. Alternatively, water and the particular glycol may be mixed prior to the addition of the alginate. Furthermore, the drug may be added to the water/glycol mixture prior to the addition of the alginate.

Sodium alginates gel by cross-linking between a pH range of 3 to 5. Calcium chloride has been selected for its low pH and in vivo biocompatible characteristics to cross-link the algin gel creating a strong film. Alginates, when cross-linked with calcium chloride form a biodegradable/bioabsorbable film that is lubricious and thus provides a lubricating coating. This lubricious coating can assist in the insertion of the medical device into the human body.

Sodium alginate used in the embodiments of this invention may also include Monsanto Keltone HVCR. A formulation was prepared from the HVCR grade that represents the mannuronic acid and guluronic acid content that will produce suitable solutions of algin and is similar in characterizations to Monsanto part number K8P569 and ProNova part number UP MVG which is the most preferred alginate polymer of the invention. This solution has an acceptable viscosity, film forming rheology and film mechanical properties, and produces an in vivo biocompatible solution and film.

The alginate solution can be used to coat an implantable medical device, at its point of use, whereby the high viscosity alginate solution, to which a drug has been added, is rendered into a film by dipping the coated device into calcium chloride. To restrict the film to the exterior and perforations of a device, the internal diameter of the device can be blocked off, for example with a balloon, during the coating process. Over an extended period of time, through its biodegradable characteristics, the film can deliver a controlled amount of a drug that was added to the alginate solution at the point of use, in known concentration over such extended period of time. The drug may be delivered either uniformly or nonuniformly depending on the uniformity of the coating thickness.

For the following examples, non-sterile Monsanto alginate part number HVCR was used whose properties are comparable to the purified form Monsanto part number K8P569 alginate and ProNova part number UP MVG.

In order to produce a biocompatible conformal film solution, application of Good Manufacturing Procedures (GMP) and use of sterile, low endotoxin sodium alginate and sterile, low endotoxin 10% calcium chloride solutions, are recommended to ensure raw material and finished product quality.

In the preferred embodiment of this invention, sodium alginate is mixed with sterile, low-pyrogen water, which is also known as "water for injection," to form a solution. Sodium alginate concentration amounts of about 1% to about 8% by weight and of various molecular weights, in the range of 12,000 to 190,000 with a preferred molecular weight of 120,000 to 190,000 can be used to form a pourable solution tailored to rheological properties desired for the application.

Proper blending techniques are necessary to dissolve the lyophilized sodium alginate in water. A high-shear mixer, which creates vortex, is recommended. The mixing blade is placed off center in the mixing container. The mixing blade is positioned near the bottom of the solution to avoid introducing excessive air. The lyophilized alginate is slowly sifted into the vortex. The application of heat aids in dissolving the alginate powder. While blending, slowly elevate the heat to 135 degrees Fahrenheit and mix for approximately 30 minutes.

The following examples illustrate preferred compositions and formulations that can be used to prepare solutions of alginate, suitable for use in medical implant procedures.

Using the manufacturing procedures outlined above, two solutions of alginate were prepared to determine its physical film properties. The following examples were prepared:

EXAMPLE 1 PART A PART B

| PART A | PART B |
|---|---|
| 8% Grade HVCR sodium alginate 92% sterile low-pyrogen water | 10% Calcium Chloride Solution |

EXAMPLE 2

| PART A | PART B |
|---|---|
| 4% Grade HVCR sodium alginate 96% sterile low-pyrogen water | 10% Calcium Chloride Solution |

The most preferred formula for the embodiment of this inventive device of an in vivo biodegradable conformal film system is the formula used in Example 2 that utilizes 4% sodium alginate (Part A).

Once the alginate polymer solution (in either liquid or gel form) has been prepared by the addition of the polymer to the initial liquid (e.g. water or water and propylene glycol), a drug can be added at the point of use through mixing into the solution. Alternatively, a drug may be added to the liquid to which the polymer is then added to form the solution. A device is then dipped into the solution, coating the device with the drug impregnated solution. Alternatively, the solution may be painted or sprayed onto the device. As previously stated, to restrict the film to the exterior and perforations of a device, the internal diameter of the device can be blocked off, for example with a balloon, during the coating process. The device is then place into sterile, pyrogen-free 10% calcium chloride (Part B) for up to ten minutes, cross-linking the gel and forming a strong, elastic film.

In the above experiments, the elasticity of the film created exceeded 200%. This elasticity makes the film ideal for implantable devices that are expanded once placed at the desired location (i.e., vascular stent).

The invention can be achieved using polymer systems other than alginates such as polymer systems which are in vivo biocompatible and biodegradable and cured with light, such as ultraviolet, or simply dried to form a film. For example, biodegradable PEG polymer (polyethylene glycol) or its derivatives and copolymers that are cured by exposure to ultraviolet light at the point of use may be utilized. Polymers of this nature are commercially available, for example, from Shearwater Polymers of Huntsville, Ala. and are supplied as dry powders that are water soluble and can be mixed with sterile water, or other biocompatible solvents, at the point of use. Bonding of a PEG polymer drug bearing film to a device can be enhanced by the presence of an amino group on the surface which anchors the conformal film.

The invention can also be achieved using previously-mentioned hydrogels such as thermal irreversible hydrogels that are in vivo biocompatible and biodegradable. One example is a PEO/PEG polymer (e.g. Pluronic manufactured by BASF) combined with an alginate, such as sodium alginate, mixed with water to form a solution and cross-linked by interaction with calcium ions (e.g. immersion in 10% by weight calcium chloride). Hydrogel containing films may exhibit less elasticity than the cross-linked sodium alginate films discussed above. However, such hydrogel films are well suited as coatings for devices that are static or unexpanding, such as suture rings Although the preferred cross-linking agent is calcium chloride, other soluble- substances may be utilized. For example, calcium compounds, such as $CaSO_4$, magnesium compounds such as $MgCl$ or $MgSO_4$, or barium compounds are also contemplated by the present invention for use in cross-linking.

While the invention has been described with reference to preferred embodiments it is to be understood that the invention is not limited to the particulars thereof. The present invention is intended to include modifications which would be apparent to those skilled in the art to which the subject matter pertains without deviating from the spirit and scope of the appended claims.

What is claimed is:

1. A method of producing an implantable drug-deliverable medical device at a point of use, said method comprising:
   providing an implantable medical device,
   coating said device with an in vivo biocompatible and biodegradable or bioabsorbable or bioerodable liquid or gel solution containing a polymer, said solution comprising a desired dosage amount of one or more predetermined drugs,
   converting said liquid or gel solution to a film adhering to said medical device thereby forming said implantable drug-deliverable medical device,
   wherein the steps of coating and converting are carried out at said point of use of said implantable medical device.

2. The method of claim 1 wherein said polymer comprises sodium alginate and said solution comprises water and said sodium alginate.

3. The method of claim 2 comprising sodium alginate in an amount of about 1% by weight to about 8% by weight.

4. The method of claim 3 wherein said sodium alginate comprises a molecular weight of about 12,000 to about 190,000.

5. The method of claim 4 wherein said sodium alginate comprises a molecular weight of about 120,000 to about 190,000.

6. The method of claim 3 comprising sodium alginate in an amount of about 4% by weight.

7. The method of claim 3 wherein said sodium alginate comprises mannuronic acid in an amount by weight of 58% to 62% and guluronic acid in an amount by weight of 42% to 38%.

8. The method of claim 2 wherein said one or more drugs are non-water soluble and wherein up to about 10% of said water is replaced with propylene glycol.

9. The method of claim 1 wherein said converting comprises cross-linking said solution to form said film.

10. The method of claim 9 wherein said cross-linking is effected with a calcium chloride solution.

11. The method of claim 10 wherein said calcium chloride solution comprises about 10% by weight calcium chloride.

12. The method of claim 1 wherein said polymer comprises polyethylene oxide, polyethylene glycol and an alginate.

13. The method of claim 1 wherein said polymer comprises polyethylene glycol.

14. The method of claim 1 wherein converting said liquid or gel solution to a film comprises exposing said solution to light.

15. The method of claim 14 wherein said light comprises ultraviolet light.

16. The method of claim 1 wherein said implantable medical device comprises a stent.

17. The device of claim 1 wherein said implantable medical device comprises at least one of pacemaker, vascular graft, suture ring, implantable infusion port, implantable drug delivery pump, orthopedic hardware and appliances, and, neurological stimulating device.

* * * * *